United States Patent [19]
Davis et al.

[11] Patent Number: 6,051,802
[45] Date of Patent: Apr. 18, 2000

[54] NEEDLE BURNER APPARATUS

[76] Inventors: Warren Davis, 942 Eldorado La., Las Vegas, Nev. 89123; David Wasserman, 2095 Mohigan Way, Las Vegas, Nev. 89109; Robert Dybus, 1437 Rawhide Rd., Boulder City, Nev. 89005

[21] Appl. No.: 09/120,263

[22] Filed: Jul. 21, 1998

Related U.S. Application Data

[60] Provisional application No. 60/053,272, Jul. 21, 1997.

[51] Int. Cl.⁷ .................................................. B23K 11/22
[52] U.S. Cl. ................................................................ 219/68
[58] Field of Search ................................................. 219/68

[56] References Cited

U.S. PATENT DOCUMENTS

| | | | |
|---|---|---|---|
| 4,363,950 | 12/1982 | Mateja et al. | 219/69.11 |
| 4,605,581 | 8/1986 | Stevens et al. | 310/249 |
| 5,138,124 | 8/1992 | Kirk et al. | 219/68 |

FOREIGN PATENT DOCUMENTS

96/38255  12/1996  WIPO .

*Primary Examiner*—Geoffrey S. Evans
*Attorney, Agent, or Firm*—John Edward Roethel

[57] ABSTRACT

A needle burner apparatus is a generally rectangular box with a needle alignment plate located under the cover thereof. The interior of the box is provided with the electrode assembly, the drive assembly for horizontally rotating and horizontally reciprocating the electrode, the exhaust fan assembly and the container for collecting burned needle residue. The needle alignment plate is mounted to the underside of the cover of the box and is spring-biased upwardly. The electrode is a single rod element that is positioned horizontally in a carriage. The rod electrode is mounted for rotation along its horizontal axis and the carriage is also mounted for horizontal reciprocal motion. A drive motor effect the axial rotation of the electrode and, through a gearing assembly, the same drive motor also effects the horizontal reciprocal motion of the carriage. An exhaust fan with a charcoal filter treats any noxious fumes created by the burning or melting of the end of the needle before the fumes are exhausted from the interior of the needle burner assembly. A container is positioned below the electrode to collect any ashes or other residue created during the burning of the end of the needle.

15 Claims, 8 Drawing Sheets

NEEDLE BURNER APPARATUS

CROSS-REFERENCE TO RELATED APPLICATIONS

This application is related to and is a Continuation-in-Part of Provisional application Ser. No. 60/053,272, filed Jul. 21, 1997, entitled "Needle Burner."

This invention relates to a needle burner apparatus, and more particularly to a needle burner apparatus that controls the needle as it is driven into the burning zone and includes an exhaust fan and charcoal filter system for handling noxious fumes and gases generated during the needle burning process.

BACKGROUND OF THE INVENTION

Health and safety regulations require hypodermic needles to be properly disposed of so that used needles cannot be reused and to the lessen the risk of transmission of communicable diseases such as hepatitis and AIDS. Various devices have been proposed to address these concerns. For example, U.S. Pat. No. 4,485,918 (Mayer) discloses a needle disposal apparatus that allows the resheathing of a hypodermic needle as well as a container for the storage and disposal of the hypodermic needle after the needle has been resheathed.

Other devices have been proposed to render the hypodermic needle unusable prior to disposal. There are prior art needle disposal apparatuses that burn the needle by placing the end of the needle between two electrodes. The positioning of the end of the needle between the two electrodes causes electricity to arc from the electrodes to the end of the needle. The voltage being carried by the electrodes causes the end of the needle to be burned or melted. With the opening in the end of the needle being closed by this arcing from the electrode, the needle may then be safely disposed of.

Representative of these needle burner devices are the apparatuses shown in U.S. Pat. No. 4,628,469 (Ch'ing-Lung) which shows a container that receives the needle head through an opening in the cover thereof. As the needle head is inserted into the interior of the container, the needle head comes into contact with a pair of electrodes. The needle head completes the circuit between the pair of electrodes and the current flowing through the needle head melts the head of the needle closing the opening therein and rendering the needle unusable. Similar needle burning devices are shown in U.S. Pat. No. 4,877,934; U.S. Pat. No. 4,961,541; and U.S. Pat. No. 4,965,426.

There are drawbacks to these prior art needle burners. In order to introduce the needle between the electrodes, the needle is usually manually inserted into the needle burner. While a needle guide is used to assist in the introduction of the needle, the fact that the needle is manually inserted means that the depth of insertion of the needle is dependent on the ability and attention of the operator. If the needle is not inserted to the required depth to reach the electrodes, the end of the needle with the opening will not be properly burned and the needle may remain usable. Even if the needle is inserted to the required depth to reach the electrodes, the needle may not be held between the electrodes long enough to achieve the required degree of melting to completely close the opening in the end of the needle.

Additionally, premature wear of the electrode can occur since, in most prior art devices, the electrode remains stationary and the end of the needle contacts the same location on the electrode each time a needle is inserted for burning.

The burning of the end of the needle between the electrodes may also emit noxious or harmful fumes depending on the material from which the needle is made or depending on the residue of the liquid remaining in the needle after its hypodermic use. Unless these fumes are handled in a safe and careful manner, a health hazard may exist in the vicinity of the needle burner.

It is an object of the present invention to provide an improved needle burner apparatus that controls the insertion of the needle into contact with the electrode to ensure that proper burning of the needle is accomplished and to prevent premature wear of the electrode.

It is a further object of the invention to provide an improved needle burner apparatus that handles the noxious or harmful fumes that are created during the process of burning the end of the needle.

It is a feature of the present invention to provide a needle burner apparatus that includes an electrode that rotates about a horizontal axis and also reciprocates horizontally to continuously provide a varying contact point between the end of the needle and the electrode.

It is also a feature of the present invention to provide a spring-biased needle insertion plate to control the depth of penetration of the end of the needle as the needle comes into contact with the electrode.

It is a further feature of the present invention to provide a needle burner apparatus that includes an exhaust fan with a charcoal filer to control and treat any noxious or harmful fumes that may be generated during the needle burning process before the exhaust gases are released to the surrounding area.

It is an advantage of the present invention that the needle burning process will be controlled to ensure that the end of each needle is properly burned and closed off so that the needle will not be reusable and that any noxious or harmful fumes generated during the needle burning process will be filtered prior to being exhausted from the interior of the needle burning apparatus.

Other objects, features and advantages of the present invention will become apparent from a consideration of the following detailed description.

SUMMARY OF THE INVENTION

The needle burner apparatus comprises a generally rectangular box with a needle alignment plate located under the cover thereof. The interior of the box is provided with the main working components of the present invention: the electrode assembly, the drive assembly for rotating and horizontally reciprocating the electrode, the exhaust fan assembly and the container for collecting burned needle residue.

The needle alignment plate is mounted to the underside of the cover of the apparatus and is spring-biased upwardly. The use of a spring bias on the needle alignment plates requires the user to push the needle down in order for the end of the needle to contact the electrode and prevents inconsistent burning of the needle. The alignment plate also ensures that the needle properly engages the electrode and prevents the end of the needle from being misaligned with the electrode.

The electrode is a single rod element that is positioned horizontally in a carriage. The rod electrode is mounted for rotation along is horizontal axis and the carriage is also mounted for horizontal reciprocal motion. A drive motor effect the axial rotation of the electrode and, through a cam assembly, the same drive motor also effects the horizontal reciprocal motion of the carriage.

An exhaust fan with a charcoal filter treats any noxious fumes created by the burning or melting of the end of the needle before the fumes are exhausted from the interior of the needle burner assembly. A container is positioned below the electrode to collect any ashes or other residue created during the burning of the end of the needle.

DETAILED DESCRIPTION OF THE PREFERRED EMBODIMENTS

Figure 1:
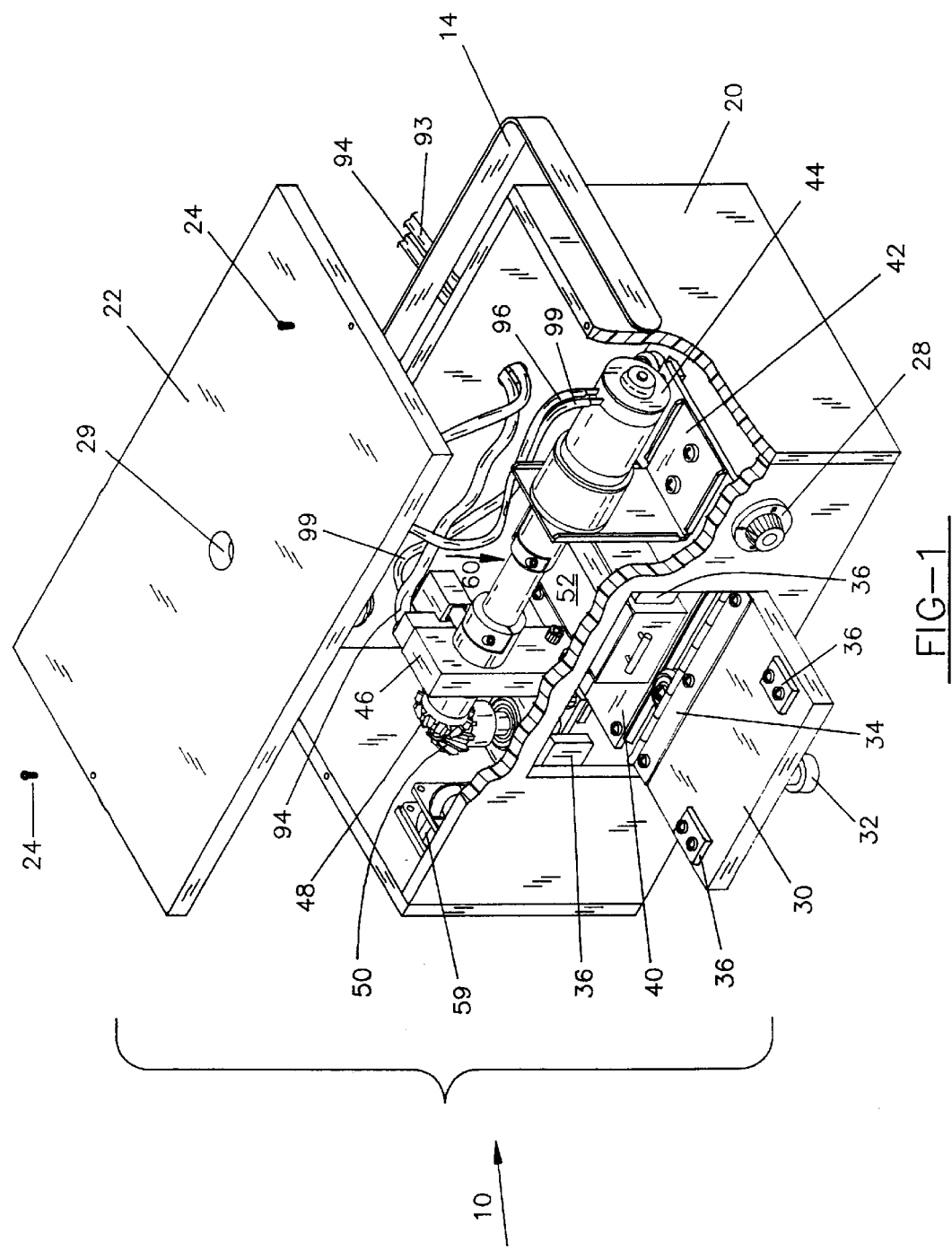
FIG. 1 shows an exploded isometric view of the needle burner apparatus of the present invention.

The needle burner apparatus of the present invention is shown generally at 10 in FIG. 1. In the preferred embodiment, the needle burner apparatus 10 comprises a generally rectangular box 20 closed on top by a lid 22 and closed at the bottom by a base 26 (see FIG. 2). The lid 22 is held in place by one or more screws 24. The box 20 and lid 22 are preferably made of plastic material so as to avoid the need for electrical insulation, but other appropriate material can be used as long as any metal parts are insulated from the electrical power supply, the electrode, the fans and the drive motor. At an appropriate location on the face of the lid 22 there is provided a needle insert aperture 29 which will receive a needle (not shown) in the operation of the needle burner apparatus 10 as will be described below. If desired, the box 20 can be provided with a carrying handle 14.

The interior of the box 20 (see FIGS. 1 and 2) is provided with the main working components of the present invention: the electrode assembly 60, the drive motor 44, an exhaust fan 59 and the cam assembly 100.

In one of the preferred embodiments of the present invention, power is supplied to the box 20 from an AC power source such as a conventional 110V outlet which is converted in any conventional manner to a direct current to operate the drive motor 44 and to power the electrode assembly 60. Alternatively, the box 20 can be configured to use one or more batteries as the power supply. The front of the box 20 can also be provided with a timer switch 28 so that the assembly can be set to run for a specified length of time.

Access is also provided to the interior of the box 20 by means of an access door 30 provided with a door handle 32. The access door 30 is preferably mounted to the front of the box 20 by a hinge 34 and one or more magnets 36 are used to secure the access door 30 in a closed position during use of the needle burner 10.

Figure 2:
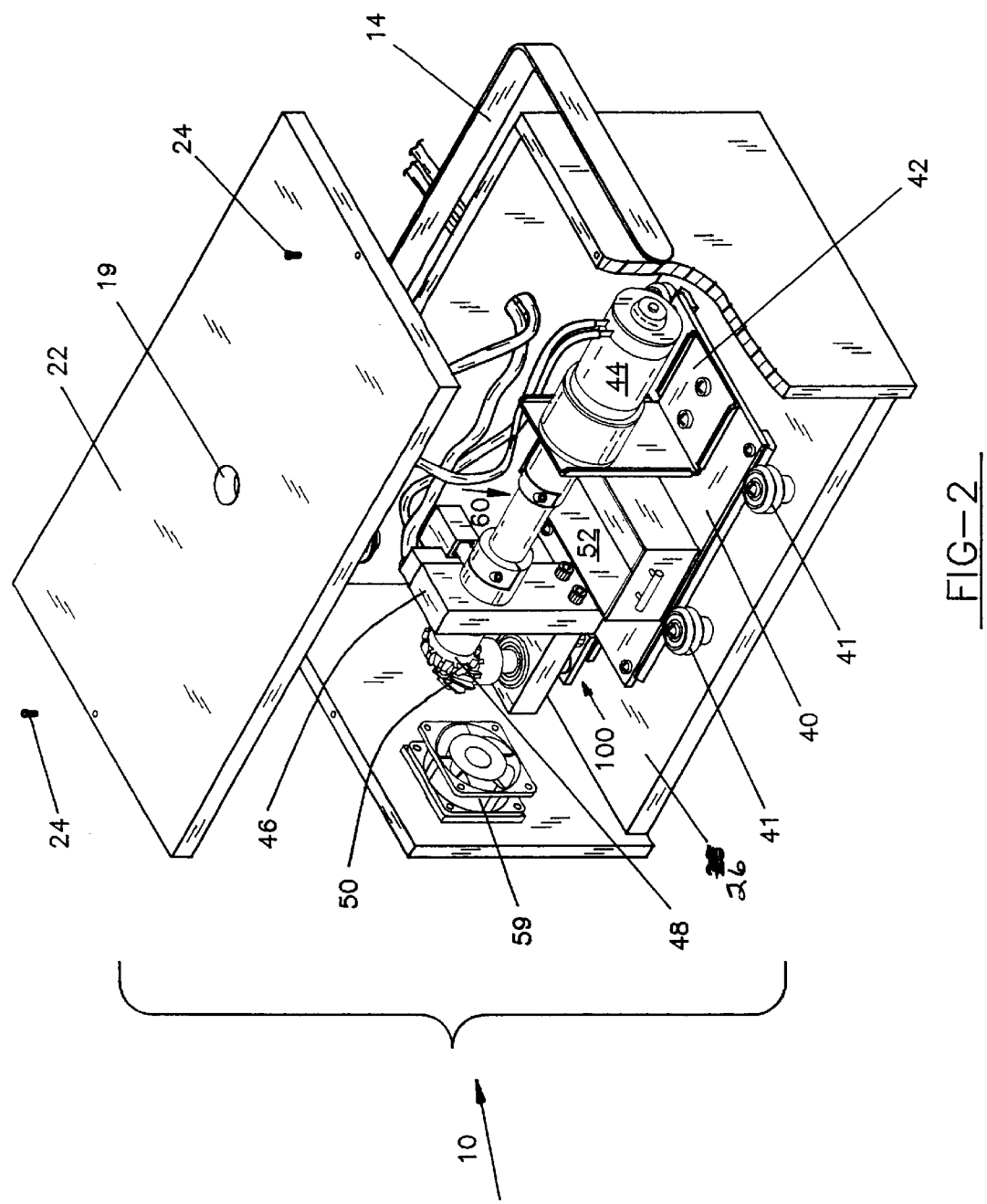
FIG. 2 shows an exploded isometric view of the needle burner apparatus of the present invention with the front of the box removed to show the details of the interior of the box.
Figure 3:
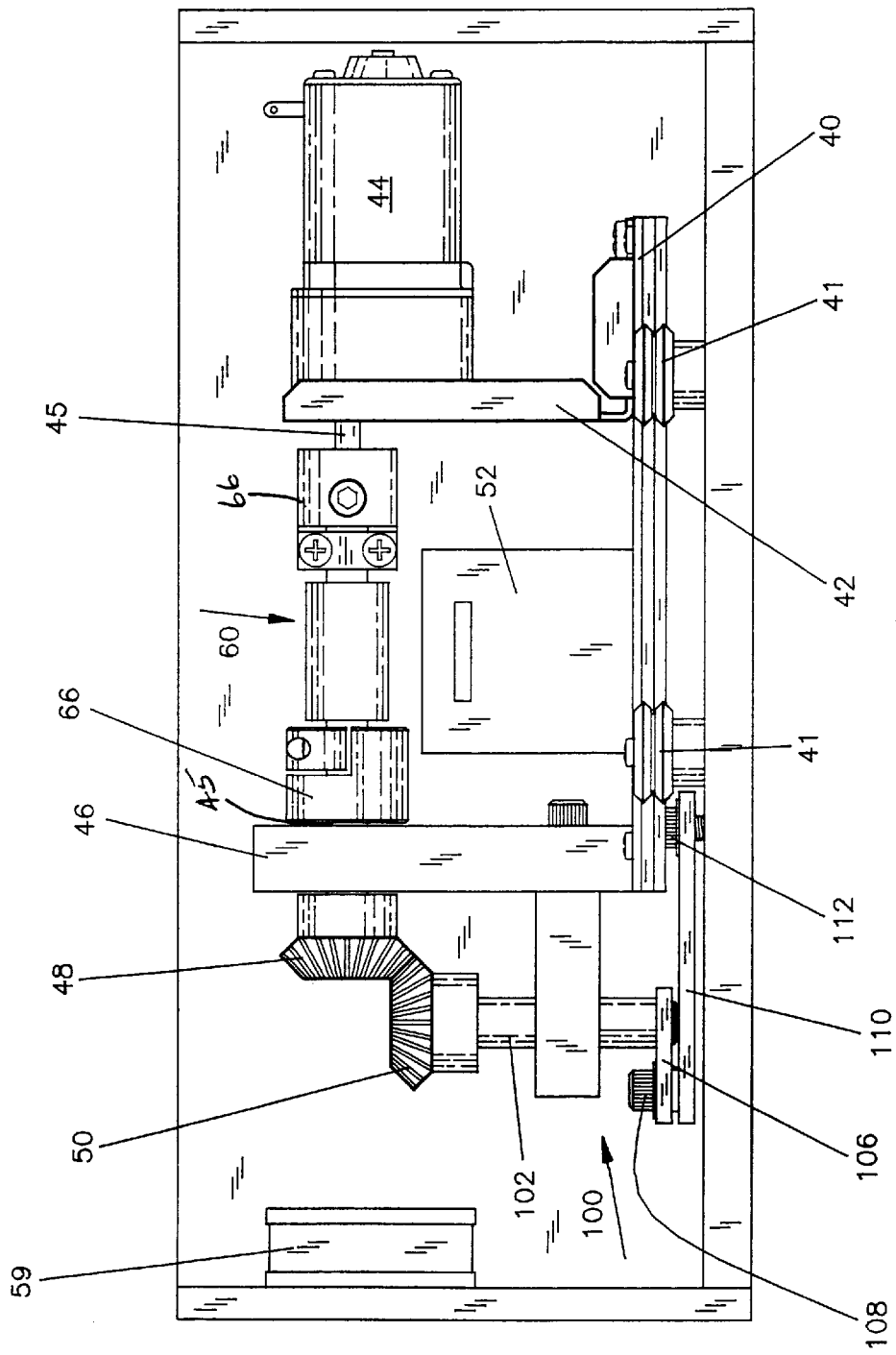
FIG. 3 shows a side view looking into the interior of the box showing the details of the present invention.
Figure 4:
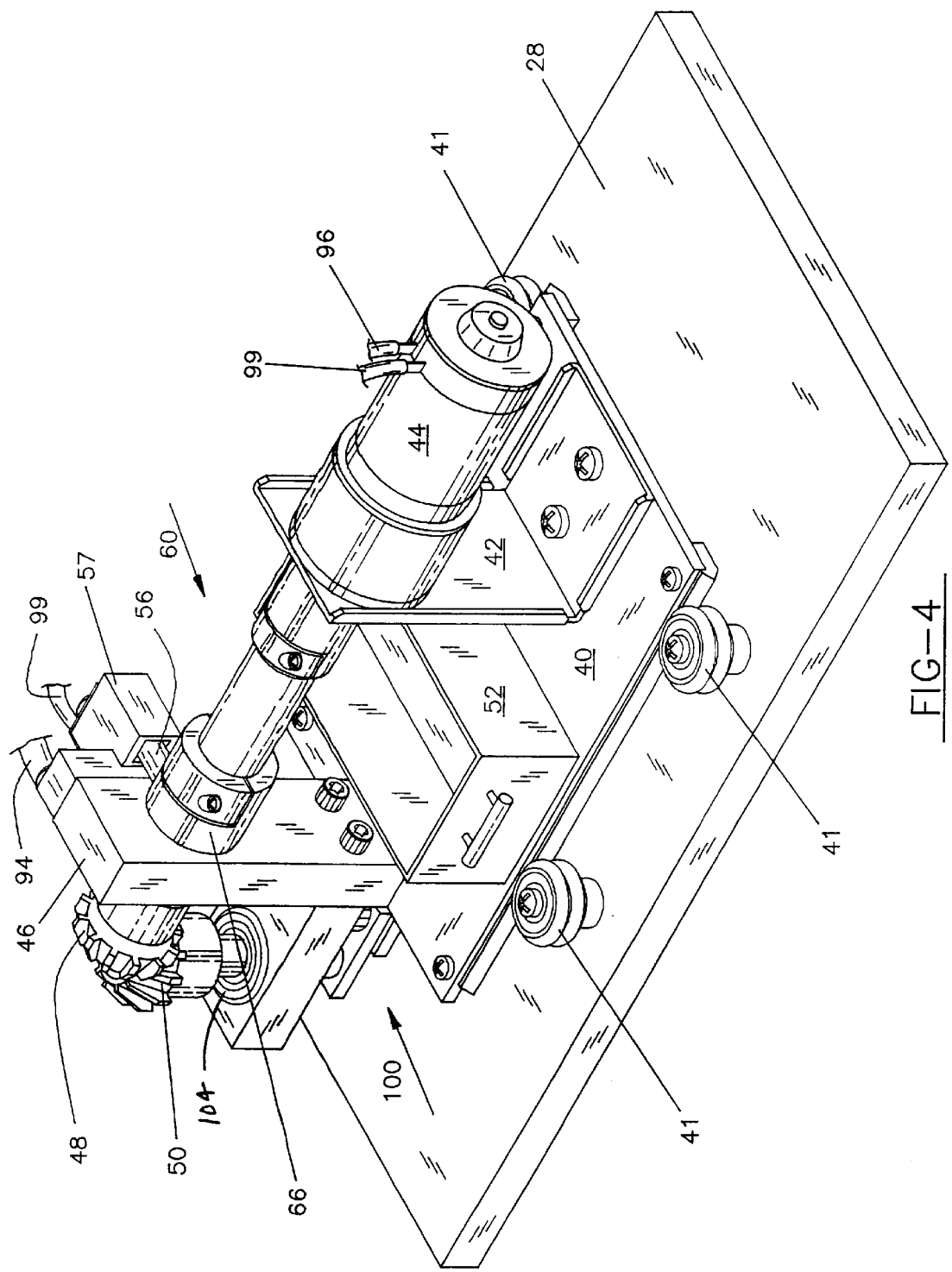
FIG. 4 shows an isometric view of the components of the present invention that are mounted on the interior of the box.

As shown more clearly in FIGS. 2, 3 and 4, the bottom interior of the box 20 has a mounting plate 40 mounted between four guide rollers 41 mounted to the base 26 which allow the mounting plate 40 to move horizontally back and forth. The mounting plate 40 carries the motor 44, the horizontal bevel gear 48, the ash container 52 and the electrode assembly 60.

One end of the mounting plate 40 has an L-shaped motor bracket 42 upon which is mounted the motor 44. The other end of the mounting plate 40 has an electrode bracket 46 and the electrode assembly 60 is positioned between the motor bracket 42 and the electrode bracket 46. A horizontal shaft 45 extends from the motor 44 through the motor bracket 42 and into a slip ring 66 on one end of the electrode assembly 60. Another horizontal shaft 45 extends from another slip ring 66 on the other end of the electrode assembly 60 through the electrode bracket 46 and terminates in a horizontal bevel gear 48. The horizontal bevel gear 48 engages a vertical bevel gear 50. Located between the motor bracket 42 and the electrode bracket 46 on the mounting plate 40 is the ash container 52.

The cam assembly 100 connects to the lower end of the vertical bevel gear 50. The vertical bevel gear 50 is mounted on the top of a vertical shaft 102. The vertical shaft 102 passes through a guide bushing 104 (see FIG. 4) and terminates at its lower end in a cam arm 106. The cam arm 106 is mounted for rotation about a pivot 108. The pivot 108 is carried on an extension arm 110 which is joined to the bottom of the mounting plate 40 at connection point 112.

When the drive motor 44 turns, the horizontal bevel gear rotates causing the vertical bevel gear to likewise rotate. This causes the vertical shaft 102 to rotate. The rotation of the vertical shaft 102 turns the cam arm 106 around the pivot 108 causing the extension arm 110 to reciprocate back and forth. This causes the mounting plate 40 to also reciprocate back and forth between the guide rollers 41. All of the elements mounted on the mounting plate 40, including the electrode assembly 60, will then also move back and forth.

Figure 5:
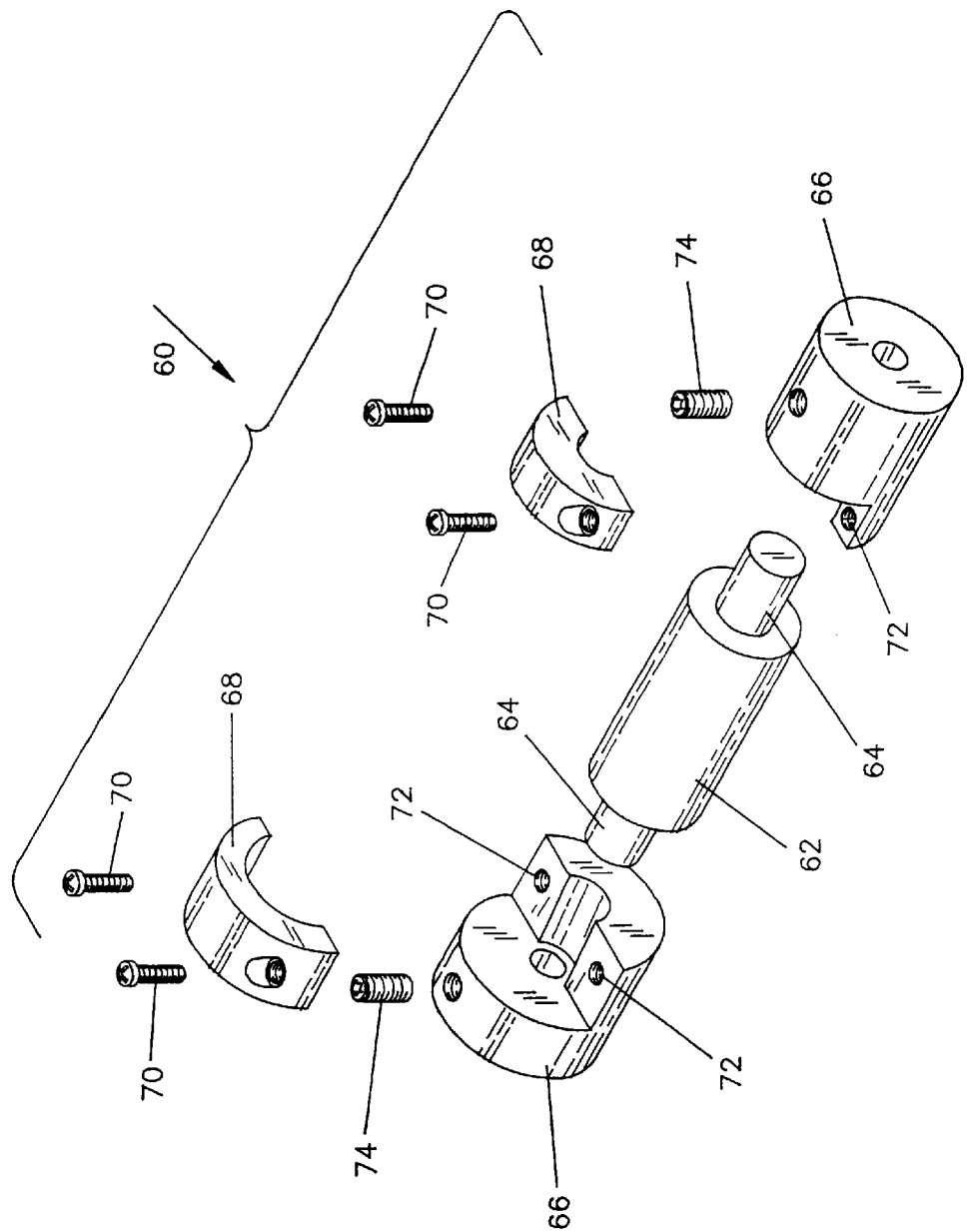
FIG. 5 shows an exploded isometric view of the electrode and its bushing assembly of the present invention.

FIG. 5 shows the details of the electrode assembly 60. The electrode assembly 60 includes a generally rod-shaped electrode 62 having an electrode shaft 64 on each end thereof. The electrode 62 can be made of any suitable electrode material, preferably carbon elements. Each electrode shaft 64 is carried for axial rotation in a slip ring 66. The electrode shaft 64 is secured in the slip ring 66 by means of an upper bushing 68 that is fastened to the slip ring 66 by one or more screws 70 that are threaded through the upper bushing 68 into an associated threaded hole 72 in the slip ring 66.

The slip ring 66 is fastened to the horizontal shaft 45 by means of a set screw 74. Thus, when the drive motor 44 rotates, the horizontal shaft 45 also rotates causing the electrode assembly 60 to also rotate. The combined action of the rotation of the electrode assembly 60 coupled with the reciprocating motion of the mounting plate 40 causes the surface of the electrode 62 to be constantly changing relative to the end of needle being brought into contact with the surface of the electrode 62.

Also connected to the electrode bracket 46 is a carbon brush 56 which is spring mounted in a brush holder 57. The spring biases the carbon brush 56 into contact with the slip ring 66.

A side wall of the box 20 is provided with an exhaust fan 59 (see FIG. 2) to remove from the interior of the needle burner 10 noxious fumes and odors which are generated during the burning of the needles. The exhaust fan 59 is preferably provided with a charcoal filter to purify the exhaust fumes before the fumes are emitted outside of the needle burner 10.

Figure 6:
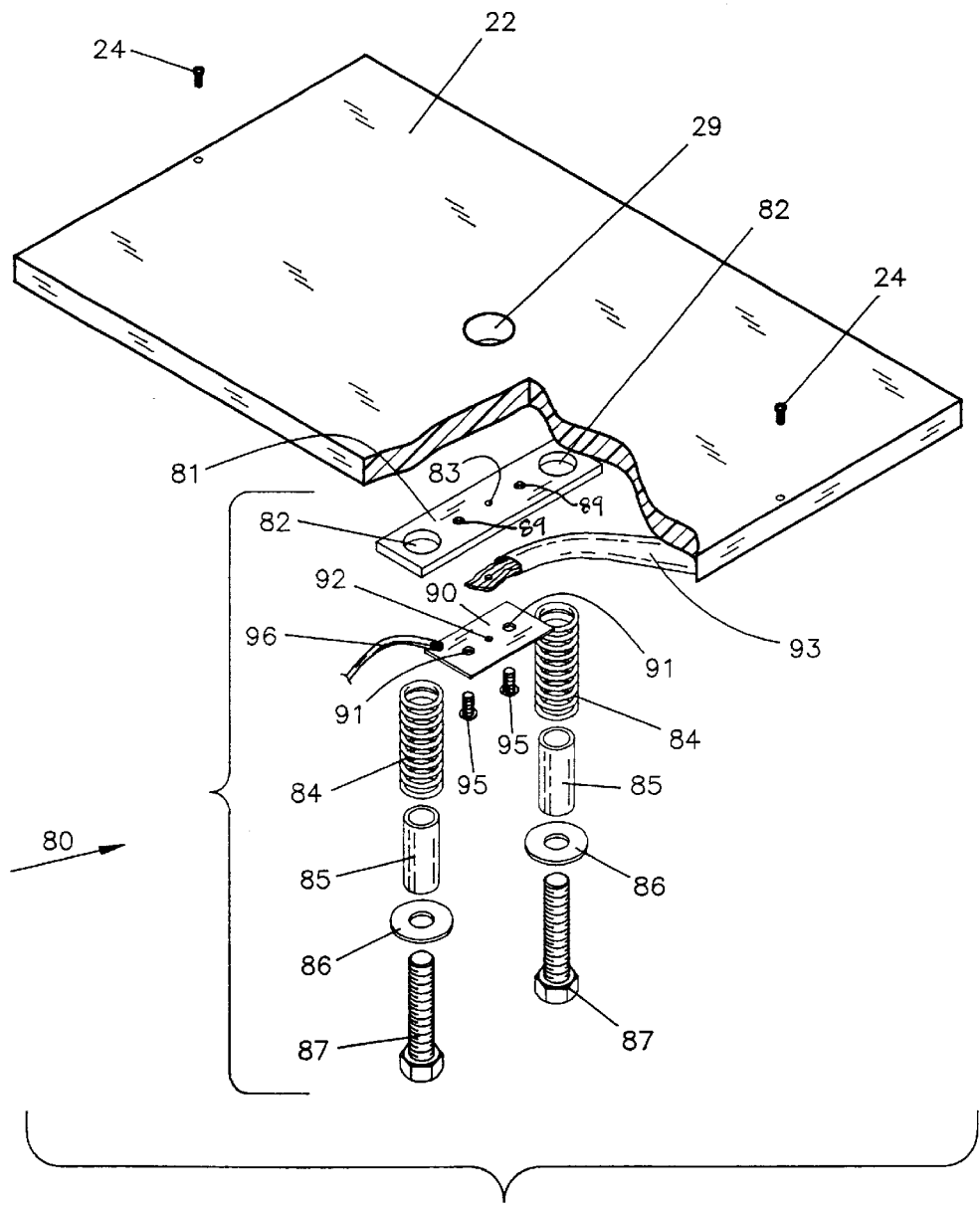
FIG. 6 shows an exploded isometric view of the lid of the box and the needle guide assembly mounted thereunder.
Figure 7:
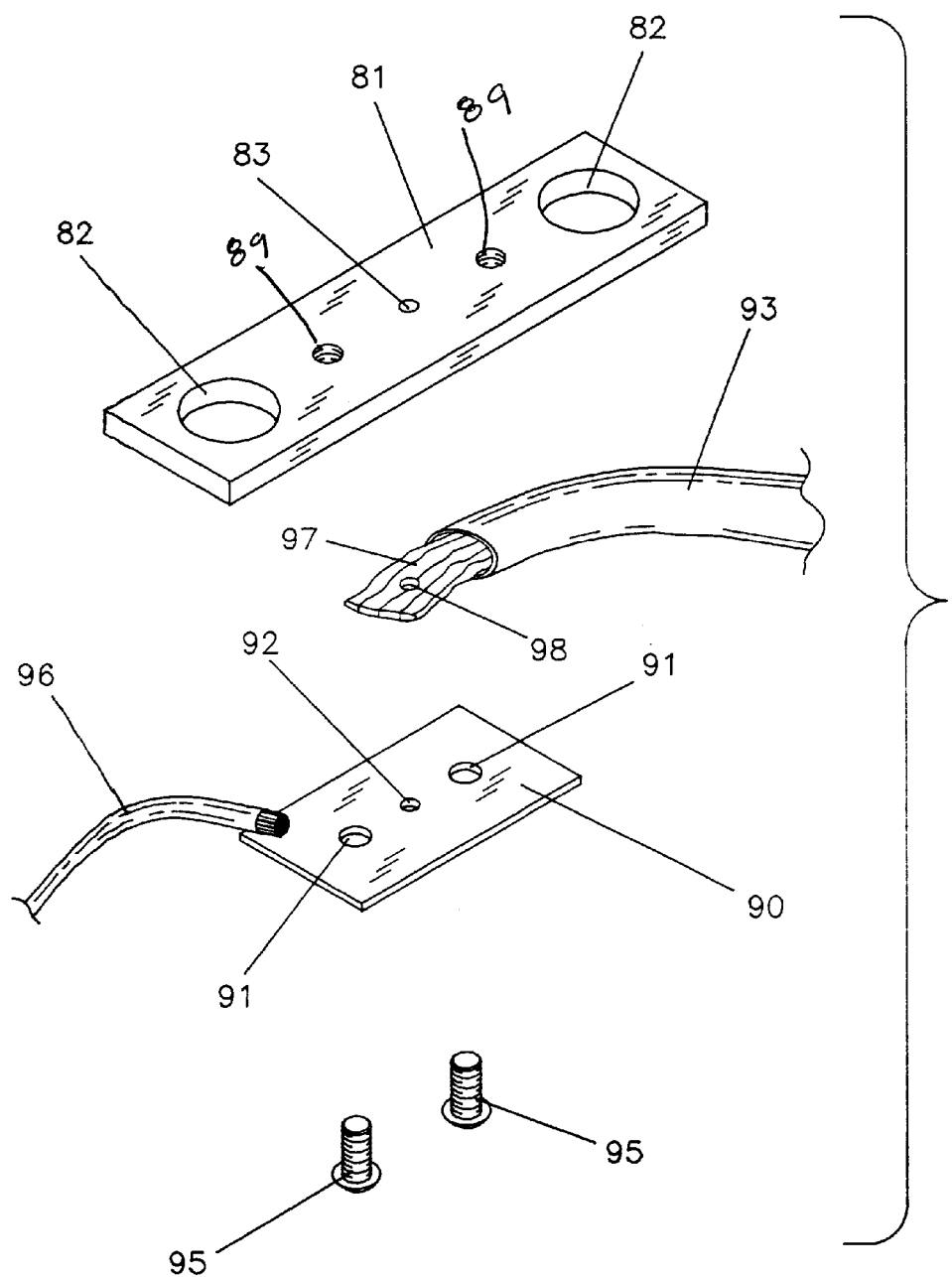
FIG. 7 shows an exploded isometric view of the alignment plate and the wire control plate.

The underside of the lid 22 of the box 20 has a needle receiving guide assembly 80 mounted thereon, the details of which are shown in FIG. 6. The needle receiving guide assembly 80 includes a alignment plate 81 that has a central needle aperture 83 that aligns with the needle insert aperture 29 in the lid 22. Each end of the alignment plate 81 has a larger bolt aperture 82 that receives the bolt 87 and allows the alignment plate 81 to ride up and down on the bolt 87. Between the head of each bolt 87 and the alignment plate 81 are provided a spring 84, a spacer 85 and a washer 86. The spring 84 function to bias the alignment plate 81 toward the underside of the lid 22. The spacer 85 sits inside the spring 84 to prevent the coils of the spring 84 from hanging up on the threads of the bolt 87. The washer 86 sits on the inside of the head of the bolt 87 and assists in maintaining the spring 84 and spacer 85 properly positioned. The threaded end of each bolt 87 is secured into the underside of the lid 22 in countersunk threaded recesses (not shown).

A wire control plate 90 is connected to the underside of the alignment plate 81 by means of one or more screws 95 which pass through an associated screw hole 91 in the wire control plate 90 and into associated threaded openings 89 in the alignment plate 81. The wire control plate 90 also has a small central screw hole 92 aligned with the needle aperture 83 in the alignment plate 81 and with the needle insert aperture 29 in the lid 22.

A first power lead 93 runs from the power source (not shown) and connects to the wire control plate 90. The termination of the first power lead 93 has the wire ends 97 exposed with an aperture 98 provided therein to allow the end of the needle to pass through. The end of the first power lead 93 is attached to wire control plate in any suitable manner such as soldering. A second power lead 94 also runs from the power supply and connects to the electrode bracket 46.

A third power lead 96 is also connected to the wire control plate 90 in any suitable manner such as soldering and runs from the wire control plate 90 and connects to the drive motor 44. A fourth power lead 99 runs from the drive motor 44 to the carbon brush 56.

The operation of the needle burner apparatus as follows. The operator sets the timer switch 28 for the desired length of time of operation. Alternatively, a proximity switch can be used instead of the timer. The proximity switch would be positioned close to the electrode 62 and the proximity switch would sense the needle being inserted. When the needle is sensed by the proximity switch, the drive motor 44 would be activated, the electrode 62 powered and the exhaust fan 59 would turn on.

The operator takes a syringe with an exposed needle to be burned and places the syringe into the needle insert aperture 29 of the lid 22. Because all of the apertures are aligned, inserting the syringe into the needle insert aperture 29 also inserts the exposed needle itself through the needle aperture 83, the aperture 98 and the needle aperture 92. The needle insert aperture 29 has a larger diameter than the diameter of the needle aperture 83 and the diameter of the needle aperture 92. Therefore, the body of the syringe comes into contact with the alignment plate 81 and the operator can force the alignment plate 81 to ride down on the bolt 87 until the exposed needle comes into contact with the electrode 62.

When the exposed needle comes into contact with the electrode 62, the exposed needle does not contact the same location on the surface of the electrode. This rotation and reciprocation motion increases the useful life of the electrode 62.

When the needle contacts the electrode 62 an electrical circuit is closed causing the electrode to burn the end of the needle. The burning of the end of the needle causes the central passageway in the needle to be closed off.

At the same time that the end of the needle 15 is being burned or incinerated, the exhaust fan 59 is running. Any noxious fumes produced during the burning or melting of the end of the needle are drawn into the exhaust fan 59 and are then exhausted from the interior of the box 20. Because the exhaust fan 59 has a charcoal filter associated therewith, the noxious fumes are treated by passing through the charcoal filter before the fumes are exhausted.

Once the end of the needle has been burned or incinerated, the operator can remove the syringe from the needle burner apparatus 10 and safely dispose of any metallic remains of the needle and the plastic syringe that may be harmful. By so doing, the need has been eliminated for a special Sharps container for syringes and needles and the remains from the needle burning can be treated as normal biohazardous waste.

The timer should be set to include the necessary time after the burning of the needle has been completed to exhaust the noxious gases. When a proximity switch is used, the exhaust fan should be set to run a additional time, say five seconds, after the needle has been burned.

During the burning of the needle, ashes and other residue may be created. This residue falls below the electrode 62 and is collected in the ash container 52. When it is desired to empty the ash container 52, the access door 30 is opened and the ash container 52 can be removed and emptied.

Figure 8:
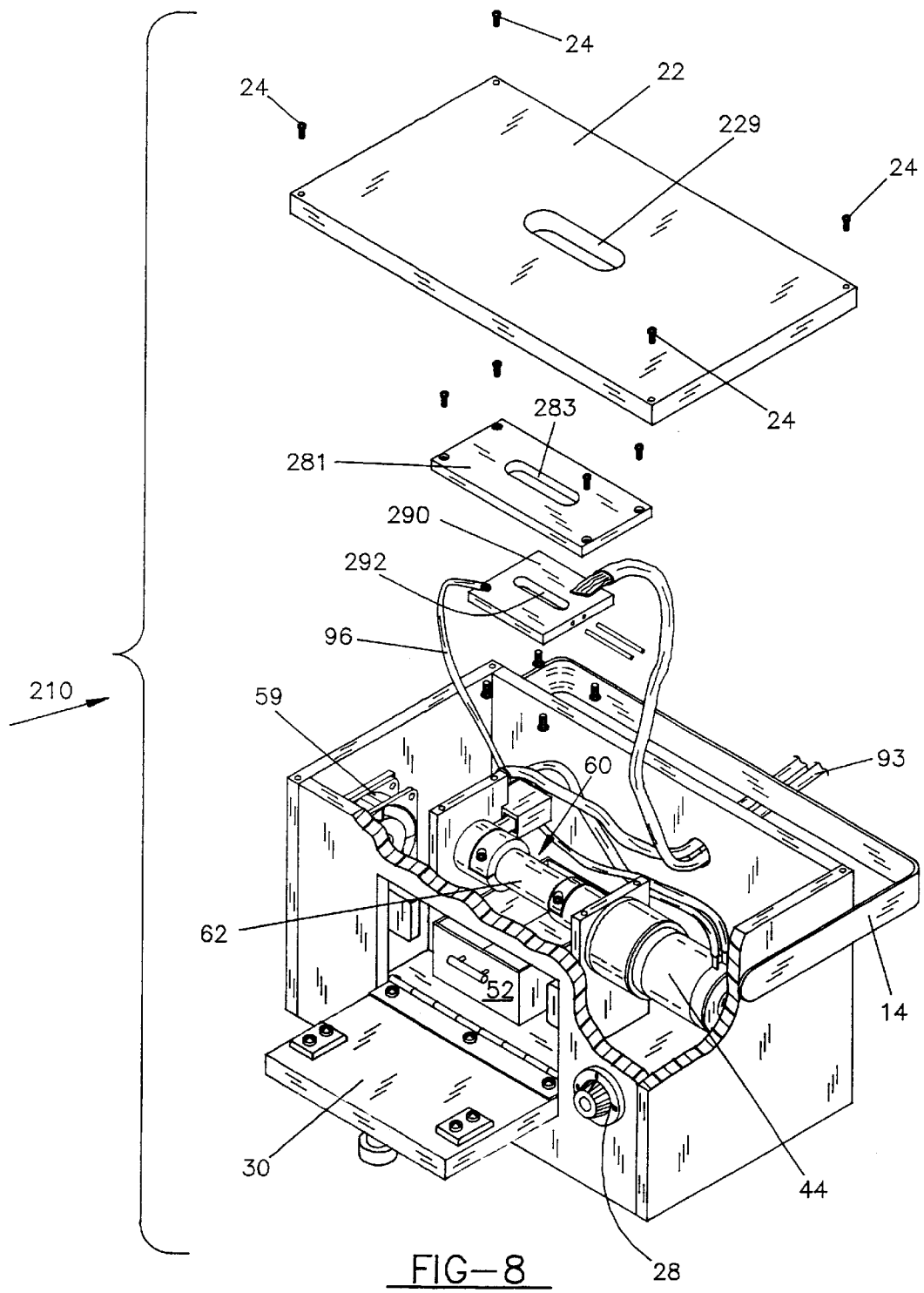
FIG. 8 shows an exploded isometric view of an alternate embodiment of the needle burner apparatus of the present invention.

An alternative embodiment of the needle burner 210 assembly of the present invention is shown in FIG. 8. Like parts in FIG. 8 have the same reference numerals as used in the previous Figures.

In this alternative embodiment, the reciprocating mounting plate 40 and the cam assembly are eliminated and the only movement of the electrode 62 is the horizontal rotation caused by the drive motor 44. Also, the alignment plate 281 is fixed to the underside of the lid 22 and does not ride up and down on bolts and is not spring biased in any manner.

The lid 22 is provided with an oblong needle insert slot 229 which aligns with an oblong needle slot 283 in the fixed alignment plate 281. Likewise, the wire control plate 290 has an oblong needle slot 292 aligned with the needle insert slot 229 and the needle slot 283.

In use, the needle burner 210 is activated by the timer switch 28. The operator inserts a syringe having a needle thereon into the needle insert slot 229, through the needle slot 283 and the needle slot 292 and into contact with the electrode 62. When the metal sides of the needle contacts the sides of the needle slot 292, an electrical circuit is completed causing a charge to be placed on the electrode 62. When the needle contacts the electrode 62 another electrical circuit is closed causing the electrode to burn the end of the needle. The burning of the end of the needle causes the central passageway in the needle to be closed off. The rotation of the electrode 62 prevents premature wear of the electrode 62.

While the invention has been illustrated with respect to several embodiments thereof, these embodiments should be considered as illustrative rather than limiting. Various modifications and additions may be will be apparent to those skilled in the art.

What is claimed is:

1. A needle burner apparatus comprising:
 a) a box having a floor and a lid, the lid including a needle insert aperture therein;
 b) a mounting plate positioned on the interior of the box and means connected to the base of the box for reciprocating the mounting plate in a generally horizontal motion;
 c) an electrode assembly attached to the mounting plate, the electrode assembly including an electrode;
 d) a power supply electrically connected to the electrode;
 e) a drive motor connected to the electrode assembly for rotating the electrode about a generally horizontal axis; and
 f) a needle receiving guide assembly mounted underneath the lid
  whereby when a needle is inserted into the needle insert aperture, the needle is guided by the needle receiving guide assembly into electrical contact with the electrode so that the needle is burned.

2. The needle burner apparatus of claim 1 wherein the means for reciprocating the mounting plate in a generally horizontal axis comprises a cam assembly mechanically joined to the drive motor through the electrode.

3. The needle burner apparatus of claim 2 wherein the cam assembly includes a horizontal bevel gear connected to the electrode, a vertical bevel gear connected to the horizontal bevel gear, a cam arm connected through a shaft to the vertical bevel gear, an extension arm connected through a pivot the cam arm, and the mounting plate connected to the extension arm, the mounting plate positioned for reciprocal motion on a plurality of guide rollers mounted to the base of the box.

4. The needle burner apparatus of claim 1 wherein the electrode assembly includes the electrode having an electrode shaft at each end thereof, each electrode shaft being mounted for rotational movement in a slip ring.

5. The needle burner apparatus of claim 4 wherein the electrode assembly further includes a carbon brush connected to the power supply, the carbon brush positioned in electrical contact with one of the slip rings.

6. The needle burner apparatus of claim 1 wherein the needle receiving guide assembly includes an alignment plate attached to the underside of the lid, a wire control plate attached to the alignment plate and a power lead attached from the wire control plate to the power supply and a power lead attached from the wire control plate to the electrode assembly.

7. The needle burner apparatus of claim 6 wherein the needle guide assembly is mounted in a spring biased position on at least one bolt whereby the needle guide assembly is spring biased toward to the underside of the lid.

8. The needle burner apparatus of claim 1 further including an exhaust fan mounted on the interior of the box.

9. The needle burner apparatus of claim 1 further including an ash container mounted on the interior of the box for collecting ash residues generated during the burning of a needle.

10. A needle burner apparatus comprising:
 a) a box having a floor and a lid, the lid including a needle insert aperture therein, the needle insert aperture being in the form of an oblong slot so that an inserted needle may be manually moved relative to an electrode;
 b) an electrode assembly positioned on the interior of the box, the electrode assembly including the electrode;
 c) a power supply electrically connected to the electrode;
 d) a drive motor connected to the electrode assembly for rotating the electrode about a generally horizontal axis; and
 e) a needle receiving guide assembly mounted underneath the lid
  whereby when a needle is inserted into the needle insert aperture, the needle is guided by the needle receiving guide assembly into electrical contact with the electrode so that the needle is burned.

11. The needle burner apparatus of claim 10 further including an exhaust fan mounted on the interior of the box.

12. The needle burner apparatus of claim 10 further including an ash container mounted on the interior of the box for collecting ash residues generated during the burning of a needle.

13. A needle burner apparatus comprising:
 a) a box having a floor and a lid, the lid including a needle insert aperture therein;
 b) an electrode assembly positioned on the interior of the box, the electrode assembly including an electrode;
 c) a power supply electrically connected to the electrode;
 d) a drive motor connected to the electrode assembly for rotating the electrode about a generally horizontal axis; and
 e) a needle receiving guide assembly mounted underneath the lid, the needle receiving guide assembly including an alignment plate attached to the underside of the lid, a wire control plate attached to the alignment plate and a power lead attached from the wire control plate to the power supply and a power lead attached from the wire control plate to the electrode assembly
  whereby when a needle is inserted into the needle insert aperture, the needle is guided by the needle receiving guide assembly into electrical contact with the electrode so that the needle is burned.

14. A needle burner apparatus comprising:
 a) a box having a floor and a lid, the lid including a needle insert aperture therein;
 b) an electrode assembly positioned on the interior of the box, the electrode assembly including an electrode having an electrode shaft at each end thereof, each electrode shaft being mounted for rotational movement in a slip ring;
 c) a power supply electrically connected to the electrode;
 d) a drive motor connected to the electrode assembly for rotating the electrode about a generally horizontal axis; and
 e) a needle receiving guide assembly mounted underneath the lid
  whereby when a needle is inserted into the needle insert aperture, the needle is guided by the needle receiving guide assembly into electrical contact with the electrode so that the needle is burned.

15. The needle burner apparatus of claim 14 wherein the electrode assembly further includes a carbon brush connected to the power supply, the carbon brush positioned in electrical contact with one of the slip rings.

* * * * *